United States Patent
Disegi et al.

(10) Patent No.: US 10,610,123 B2
(45) Date of Patent: Apr. 7, 2020

(54) EXTERNAL FIXATION SYSTEM WITH RADIO FREQUENCY SHIELDING

(71) Applicant: DePuy Synthes Products, Inc., Raynham, MA (US)

(72) Inventors: John Disegi, West Chester, PA (US); Thomas Joseph Maughan, West Chester, PA (US)

(73) Assignee: DePuy Synthes Products, Inc., Raynham, MA (US)

( * ) Notice: Subject to any disclaimer, the term of this patent is extended or adjusted under 35 U.S.C. 154(b) by 1452 days.

(21) Appl. No.: 13/837,598

(22) Filed: Mar. 15, 2013

(65) Prior Publication Data
US 2014/0275959 A1    Sep. 18, 2014

(51) Int. Cl.
A61B 5/055 (2006.01)
A61B 17/64 (2006.01)
A61B 17/00 (2006.01)
G01R 33/28 (2006.01)

(52) U.S. Cl.
CPC .......... *A61B 5/055* (2013.01); *A61B 17/6466* (2013.01); *A61B 17/6416* (2013.01); *A61B 2017/00929* (2013.01); *G01R 33/288* (2013.01); *Y10T 156/10* (2015.01)

(58) Field of Classification Search
None
See application file for complete search history.

(56) References Cited

U.S. PATENT DOCUMENTS

| 2,251,209 | A | * | 7/1941 | Stader ............... A61B 17/60 174/138 R |
| 4,046,013 | A | | 9/1977 | Green |
| 4,548,199 | A | | 10/1985 | Agee |
| 4,612,930 | A | | 9/1986 | Bremer |
| 4,889,111 | A | | 12/1989 | Ben-Dov |
| 5,281,221 | A | | 1/1994 | Tadych |
| 5,437,666 | A | | 8/1995 | Tepic |
| 5,496,314 | A | * | 3/1996 | Eggers ............ A61B 18/082 606/29 |
| 5,498,264 | A | | 3/1996 | Schlapfer |
| 5,705,014 | A | | 1/1998 | Schenck et al. |
| 5,961,528 | A | | 10/1999 | Birk et al. |
| 6,245,071 | B1 | | 6/2001 | Pierson |
| 6,284,971 | B1 | | 9/2001 | Atalar et al. |

(Continued)

FOREIGN PATENT DOCUMENTS

| CN | 1343108 A | 4/2002 |
| FR | 2338692 | 8/1997 |

(Continued)

OTHER PUBLICATIONS

Creative Global Services, Inc., "CGSTape", http://www.cgstape.com, © 2012, accessed Feb. 24, 2012, 2 pages.

(Continued)

*Primary Examiner* — Bill Thomson
*Assistant Examiner* — Shahdeep Mohammed
(74) *Attorney, Agent, or Firm* — BakerHostetler

(57) ABSTRACT

An electrical insulator is applied to a bone anchor, for instance of a bone implant, such as an external fixation frame, so as to prevent undesirable temperature increases in the bone anchor and surrounding anatomical tissue when subjected magnetic resonance imaging.

14 Claims, 5 Drawing Sheets

(56) References Cited

U.S. PATENT DOCUMENTS

| | | |
|---|---|---|
| 6,428,540 B1 | 8/2002 | Claes |
| 6,663,634 B2 | 12/2003 | Ahrens |
| 6,716,212 B1 | 4/2004 | Pickens |
| 7,527,626 B2 | 5/2009 | Lutz et al. |
| 2005/0085810 A1* | 4/2005 | Lutz .................. A61B 17/60 606/54 |
| 2008/0065068 A1 | 3/2008 | Thomke et al. |
| 2008/0275395 A1 | 11/2008 | Asbury et al. |
| 2009/0054897 A1 | 2/2009 | Gordon |
| 2010/0298827 A1 | 11/2010 | Cremer et al. |
| 2011/0112533 A1 | 5/2011 | Venturini et al. |
| 2011/0264094 A1* | 8/2011 | Cunliffe .............. A61B 17/00 606/59 |
| 2012/0209264 A1 | 8/2012 | Zandona |
| 2012/0303062 A1* | 11/2012 | Amstutz .......... A61B 17/7041 606/267 |

FOREIGN PATENT DOCUMENTS

| | | |
|---|---|---|
| JP | 61-501189 A | 6/1986 |
| JP | 2008-522103 A | 6/2008 |
| JP | 2011-098201 A | 5/2011 |
| WO | 85/03449 A1 | 8/1985 |
| WO | WO 2001/51119 A1 | 7/2001 |
| WO | 2012/107060 A1 | 8/2012 |

OTHER PUBLICATIONS

Dupont, "Kapton Film", http://en.wikipedia.org/wiki/Kapton, accessed Mar. 15, 2012, 3 pages.

Kuraray Co., Ltd., "Vectran Fibre", http://en.wikipedia.org/wiki/Vectran, accessed Mar. 15, 2012, 3 pages.

Sandid, et al., "Evaluating external fixation frame heating in the MR environment, An analysis for Synthes® —Interim Report I," Cibor Inc., Jul. 2011, 14 pages.

Luechinger, et al., "Safety evaluation of large external fixation clamps and frames in a magnetic resonance environment," Inst. Biomed. Eng., Wiley InterScience, Oct. 2006, 17-22.

Luechinger et al., "MRI Safety Evaluations of six Enternal Fixation Frames," GyroTools LLC, Mar. 15, 2011, 14 pages.

ASTM F2182-11a, "Standard Test Method for Measurement of Radio Frequency Induced Heating on or Near Passive Implants During Magnetic Resonance Imaging," Aug. 2011, 1-15.

Zaremba, et al., "FDA Guidelines for Magnetic Resonance Equipment Safety," Center for Devices and Radiological Health Food and Drug Administration, 2002, 9 pages.

Shellock, "Comments on MR Heating Tests of Critical Implants," Journal of Magnetic Resonance Imaging, Oct. 2007, 26:1182-1185.

Shellock, "Radiofrequency Engery-Induced Heating during MR Procedures," Journal of Magnetic Resonance Imaging, Jul. 2000, 12:30-36.

Ferhanoglu, et al., "MRI Compatible Pacemaker Leads," Proc. Intl. Soc. Mag. Reson. Med, vol. 13, 2005, 963.

Ladd, et al., "Reduction of Resonant RF Heating in Intravascular Catheters Using Coaxial Chokes," Magnetic Resonance in Medicine, Apr. 2000, 43:615-619.

Konings, et al., "Heating Around Intravascular Guidewires by Resonating RF Waves," Journal of Magnetic Resonance Imaging, Jul. 2000, 12: 79-85.

\* cited by examiner

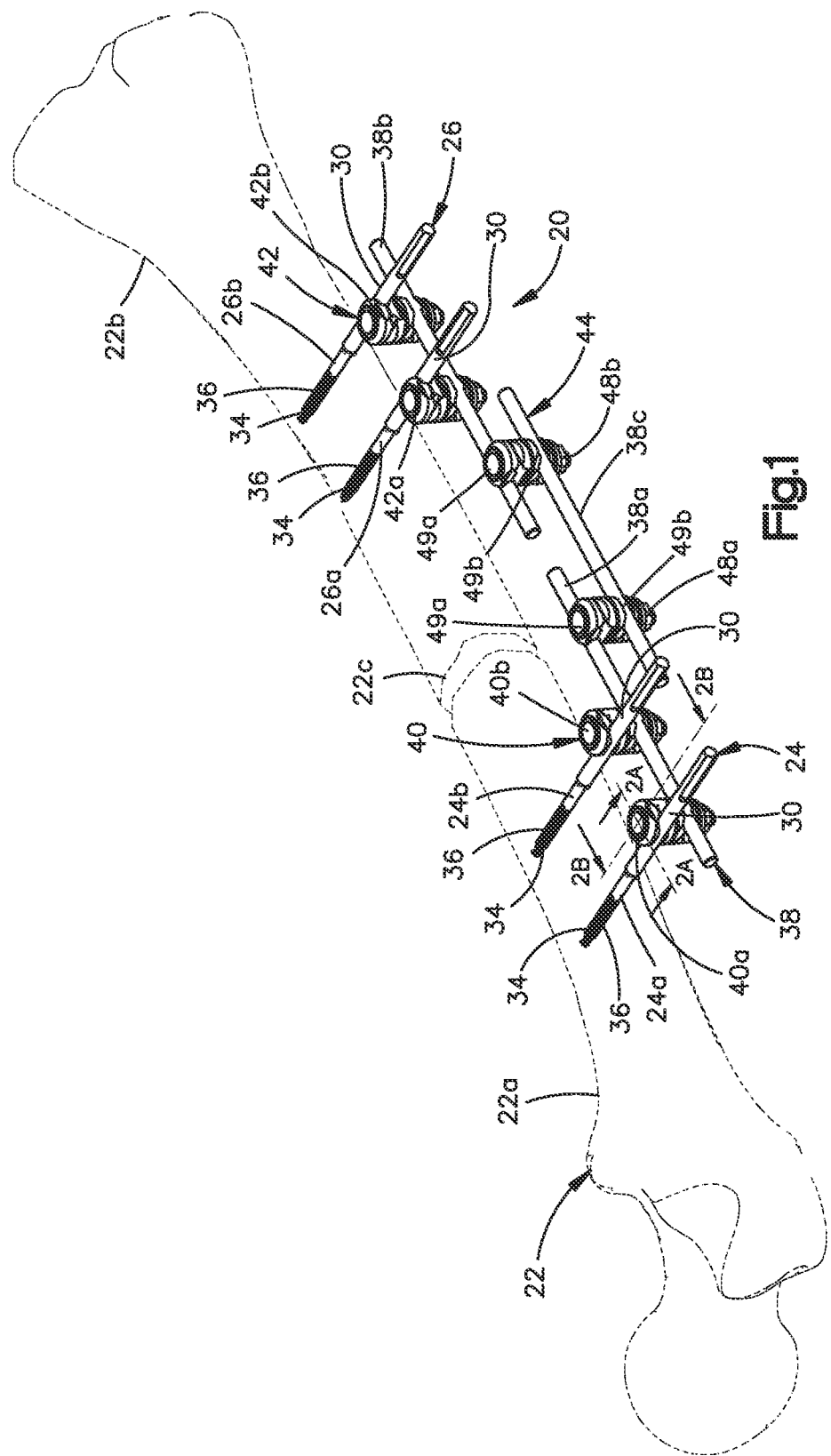

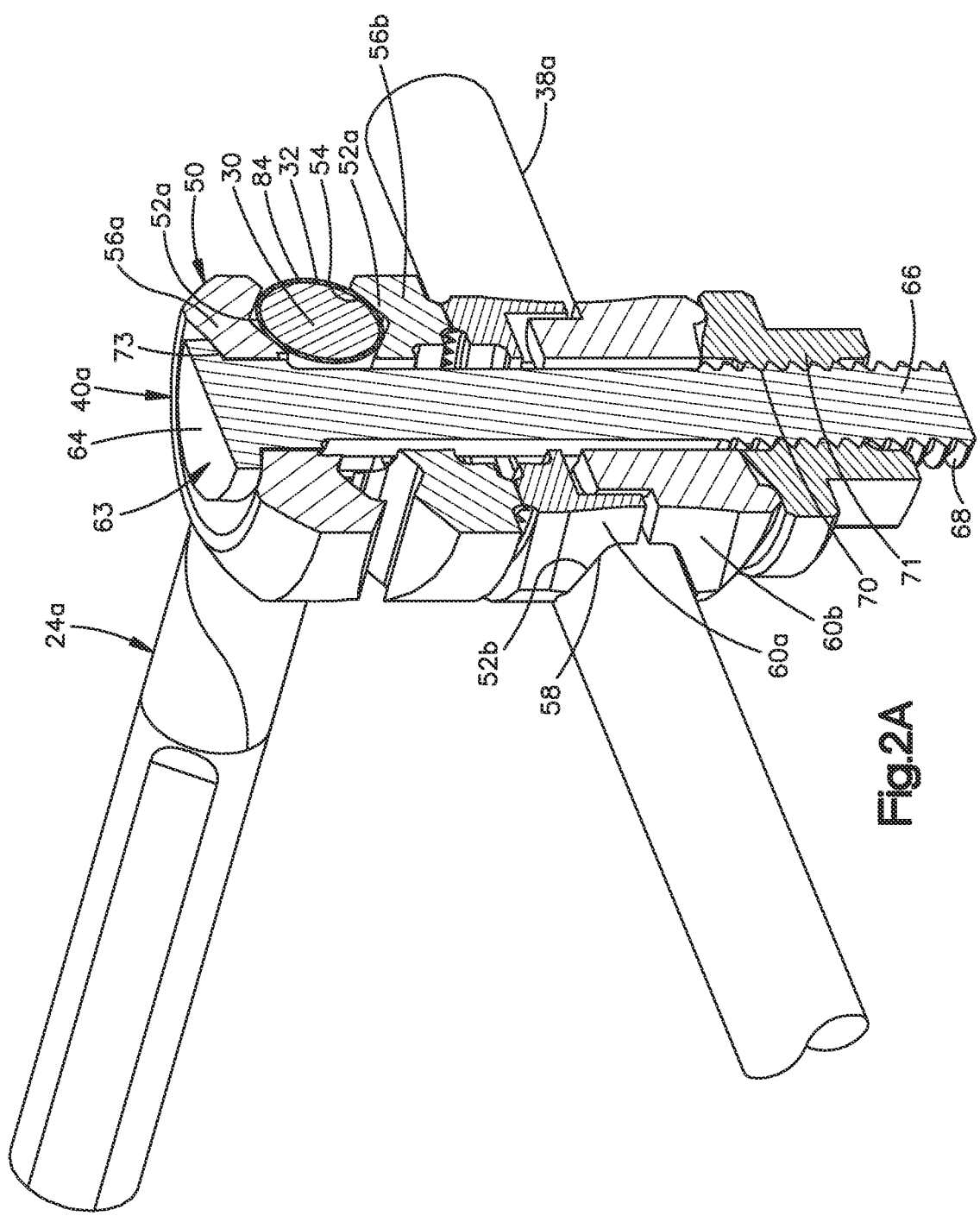

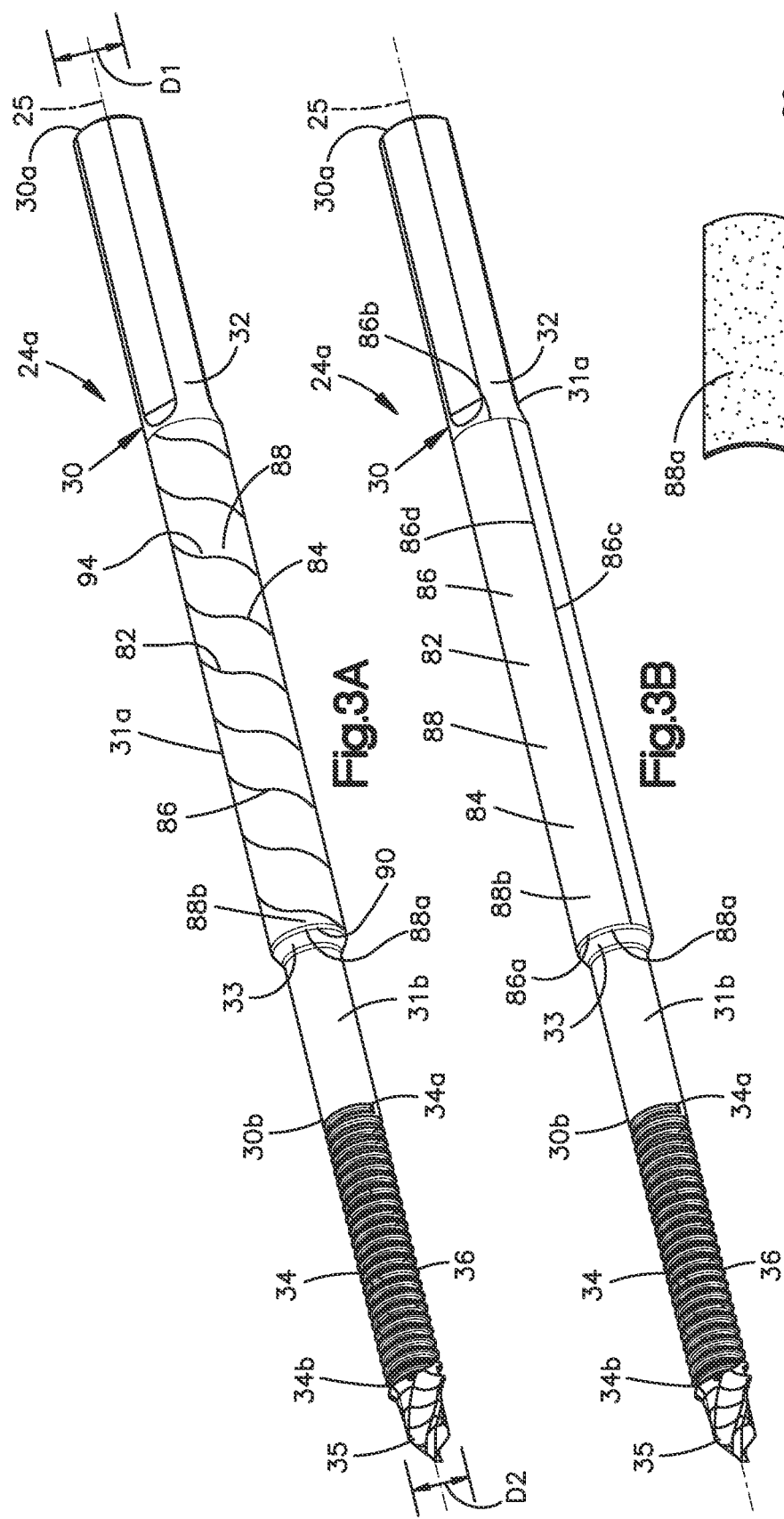
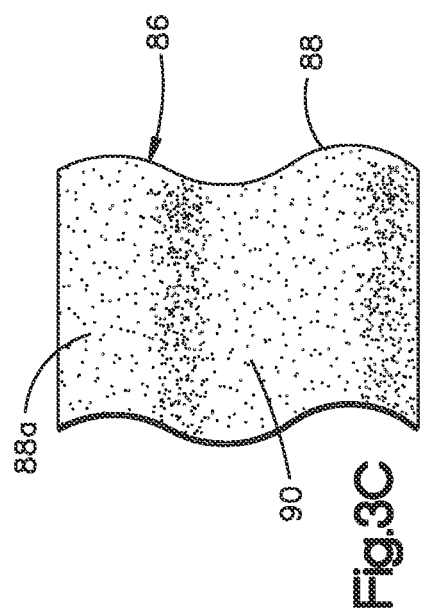

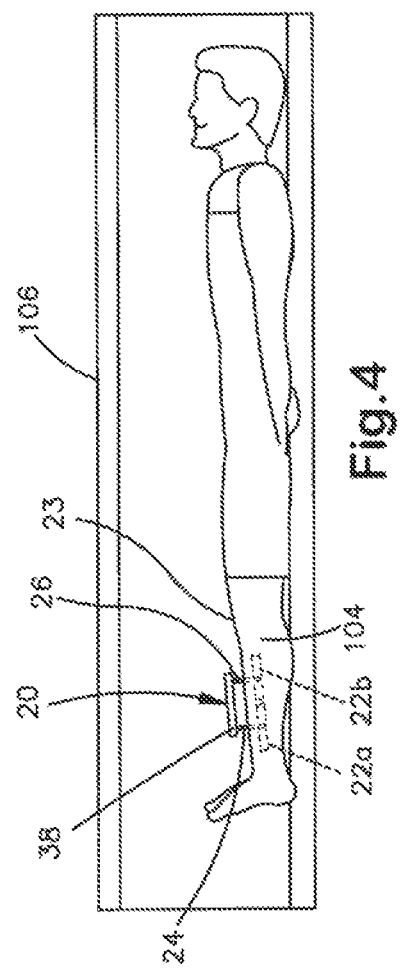

EXTERNAL FIXATION SYSTEM WITH RADIO FREQUENCY SHIELDING

BACKGROUND

Bone fixation systems can include external bone fixation systems that are typically attached to two or more bone segments so as to stabilize the bone segments and promote healing. The external bone fixation systems can be applied to treat comminuted, intra-articular and/or unstable fractures. Thus, the bone segments can be fractured segments of a bone, or can alternatively be two different bones, for instance vertebrae, that are to be stabilized relative to each other. Typical external fixation systems can include a plurality of bone anchors that are configured to be driven through the dermal surface and into respective bone segments. For instance, the bone anchors typically are configured as bone screws, such as Schanz screws, that have a length sufficient such that they extend out from the epidermis when anchored in the respective bone segments.

External fixation systems can further include at least one support rod, and at least one set of clamps that are configured to be secured to both the rod and the bone anchors, thereby securing the bone anchors relative to the rod, and supporting each the bone fixation members relative to the other bone fixation members secured to the rod. External fixation system can further include clamps that are configured to be secured to a pair of rods, so as to secure each of the pair of rods to the other. External fixation systems further commonly include coupling members that are configured to attach to both the support rod and one or more of the Schanz screws, such that the Schanz screws, and thus the bone segments, are supported by the rod in fixation with the respective bone segments.

Conventional support rods, clamps, and bone fixation members are typically made from an electrically and thermally conductive material stainless steel, titanium, alloys thereof, or any suitable alternative metal. Though support rods can be made from a non-ferromagnetic material, such as such as aluminum or carbon, the external fixation system in combination with the soft tissue into which the external fixation system is implanted can define a closed electrical loop. As a result, when the external fixation system is subjected to the magnetic fields (typically having a strength between and including 1.5 Tesla and 3.0 Tesla, but can range up to and including 8.0 Tesla) and radio frequency pulses of a magnetic resonance imaging (MRI) system, electrical current can be induced in the closed electrical loop. The current flow can cause the temperature of the thermally conductive Schanz screws to rise substantially inside the patient's body, resulting in pain and damage to the tissue.

External fixation systems have been proposed that are said to reduce or prevent current when the implanted exposed to the RF field of an MRI. For instance, U.S. Pat. No. 7,527,626 discloses that the rod and/or clamps can include a carbon core and a polymeric insulation sheath that is applied onto the carbon core through resin transfer molding. The patent recognizes that the size of the carbon core of the rod "must" be reduced so that once the sheath is applied to it, the resulting product has the same size as rods typically used in external fixation systems. Accordingly, the core is made of a higher modulus carbon fiber. Thus, the sheath can add cost and complexity to the manufacture of the external fixation system

SUMMARY

In accordance with one embodiment, an external fixation system includes a first Schanz screw including a first shaft that defines a first external surface that is devoid of threads. The first Schanz screw can further include a first threaded region that extends from the first shaft, the first threaded region presenting external threads that are configured to be anchored into bone. The external fixation system can further include a second Schanz screw including a second shaft that defines a second external surface that is devoid of threads. The second Schanz screw can further include a second threaded region that extends from the second shaft, the second threaded region presenting external threads that are configured to be anchored into bone. The external fixation system can further include at least one support rod that comprises an electrically conductive material. The external fixation system can further include a first clamp configured to attach to both the first shaft and the at least one support rod, and a second clamp configured to attach to both the second shaft and the at least one support rod, thereby fixedly supporting each of the first and second Schanz screws relative to the at least one support rod. At least the first Schanz screw can include a layer of electrically insulative material that is attached to at least a portion of the first external surface and is not attached to the first threaded region.

BRIEF DESCRIPTION OF THE DRAWINGS

The foregoing summary, as well as the following detailed description of illustrative embodiments of spreader system of the present application, will be better understood when read in conjunction with the appended drawings. For the purposes of illustrating the spreader system of the present application, there is shown in the drawings illustrative embodiments. It should be understood, however, that the application is not limited to the precise arrangements and instrumentalities shown. In the drawings:

FIG. 1 is a perspective view of an external fixation assembly shown anchored into bone;

FIG. 2A is a sectional perspective view of a portion of the external fixation assembly illustrated in FIG. 1, taken along line 2A-2A;

FIG. 3A is a perspective view of first Schanz screw of the external fixation assembly constructed in accordance with one embodiment;

FIG. 3B is a perspective view of first Schanz screw of the external fixation assembly constructed in accordance with another embodiment;

FIG. 3C is a plan view of a tape of the first Schanz screw illustrated in FIG. 3A;

FIG. 4 is a schematic illustration of a patient disposed in an MRI tube, the patient including a long bone to which an external fixation assembly of the type illustrated in FIG. 1 is attached.

DETAILED DESCRIPTION

Figure 2B:
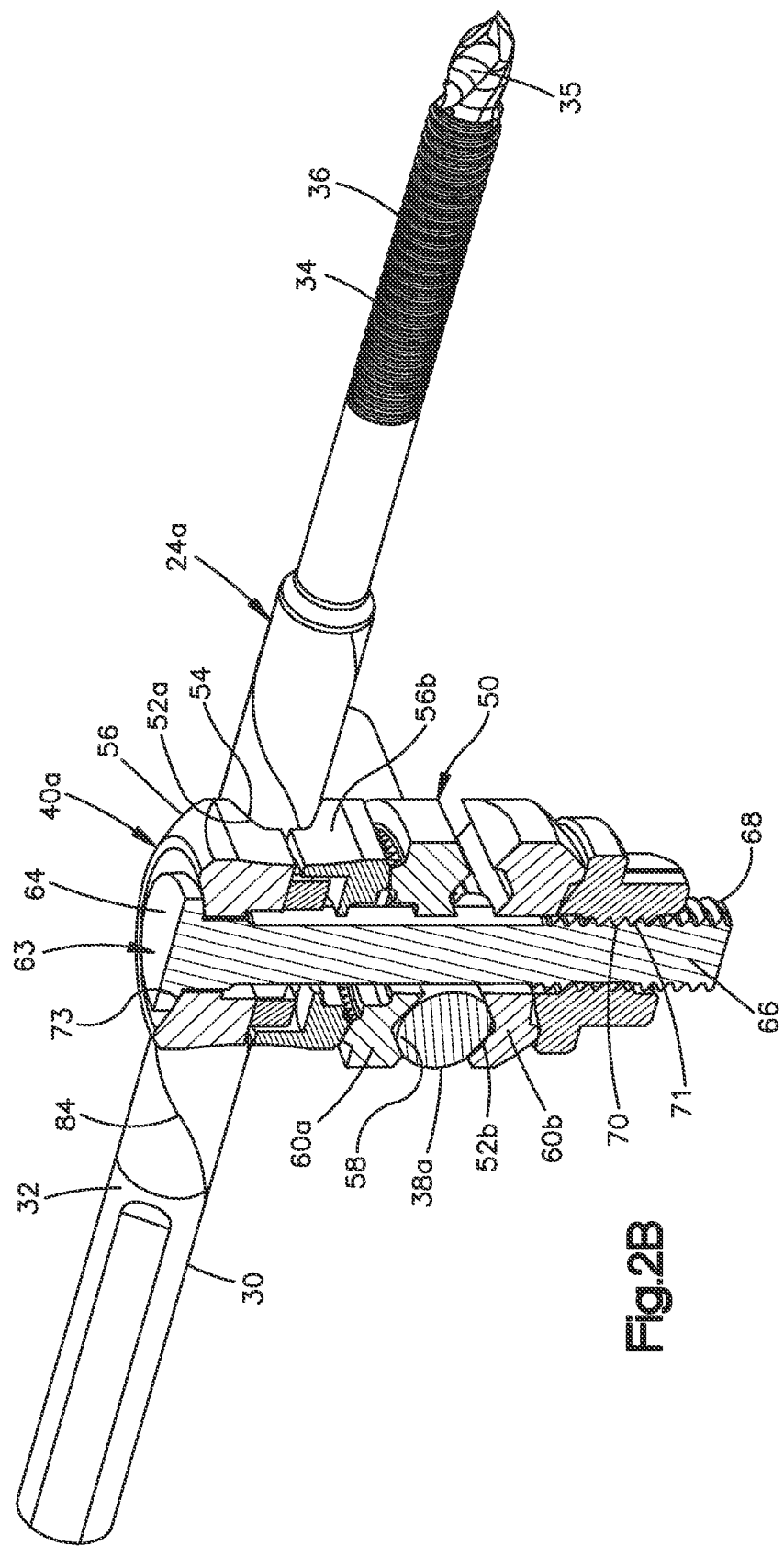
FIG. 2B is a sectional perspective view of a portion of the external fixation assembly illustrated in FIG. 1, taken along line 2B-2B.

Certain terminology is used in the following description for convenience only and is not limiting. The words "right", "left", "lower" and "upper" designate directions in the drawings to which reference is made. The words "inner" or "distal" and "external" or "proximal" refer to directions toward and away from, respectively, the geometric center of the implant and related parts thereof. The words, "anterior", "posterior", "superior," "inferior," "medial," "lateral," and related words and/or phrases are used to designate various positions and orientations in the human body to which reference is made and are not meant to be limiting. The terminology includes the above-listed words, derivatives thereof and words of similar import.

Referring to FIG. 1, a bone implant, such as an external fixation system 20, is configured to stably support a first bone segment 22a relative to a second bone segment 22b. The first and second bone segments can be of the same bone or of different bones. In accordance with the illustrated embodiment, the first and second bone segments 22a-b are of a bone, such as a long bone 22, and are separated from each other by a bone gap 22c, such as a fracture, of the long bone 22. The external fixation system 20 can include at least one external fixation bone anchor 24 configured to attach to bone, for instance at the first bone segment 22a, and at least one external fixation bone anchor 26 configured to attach to bone, for instance at the second bone segment 22b. In accordance with the illustrated embodiment, the at least one bone anchor 24 can include first and second bone anchors 24a and 24b that are configured to attach to the same bone segment, for instance to the first bone segment 22a, and the at least one bone anchor 26 can include first and second bone anchors 26a and 26b that are configured to attach to the same bone segment, for instance to the second bone segment 22b.

Thus, it should be appreciated that the external fixation system 20 can include at least a first bone anchor and a second bone anchor that are configured to be anchored into bone. The first and second bone anchors can be anchored into the same bone segment (e.g., first and second bone anchors 24a and 24b, and first and second bone anchors 26a and 26b), or can be anchored into different bone segments (e.g., first bone anchor 24a and second bone anchor 26b, and first bone anchor 26a and second bone anchor 24b). In accordance with the illustrated embodiment, each of the external fixation bone anchors 24 and 26 can be configured as screws, such as Schanz screws or K-wires, and can include a shaft 30 that defines an external surface 32 (see also FIG. 2A) that can be devoid of threads, and a threaded region 34 that extends from the shaft 30, the threaded region 34 presenting external threads 36 that are configured to be anchored into bone so as to anchor the threaded region 34 into bone. The bone anchors 24 and 26 are constructed such that, when the threaded regions 34 are driven into bone, the shafts 30 extend out from the epidermis 23 (see FIG. 4). While the bone anchors 24 and 26 are illustrated as including the threaded region 34, it should be appreciated that the bone anchors 24 and 26 can alternatively be configured as pins that are devoid of threaded regions.

While the illustrated embodiment includes first and second anchors 24a and 24b attached to the first bone segment 22a and first and second bone anchors 26a and 26b attached to the second bone segment 22b, it should be appreciated that the external fixation system can include any number of bone anchors, such as one or a plurality of bone anchors, that are configured to attach to the first and second bone segments 22a and 22b as desired. As will be appreciated from the description below, at least one, such as a plurality, up to all, of the bone anchors 24 and 26 can include at least one layer of electrically insulative material attached to at least a portion of the respective external surface 32, such that the electrically insulative material is not attached to the respective threaded region 34.

The external fixation system 20 can further include at least one support rod 38 that extend from a first location aligned with the first bone segment 22a and across the fracture location 22c to a second location aligned with the second bone segment 22b. The at least one support rod 38 is configured to be fixedly secured relative to the bone anchors 24 and 26. For instance, the at least one support rod 38 can include a first support rod 38a, a second support rod 38b, and a third support rod 38c. The first and second bone anchors 24a and 24b can be attached to the first support rod 38a, and the first and second bone anchors 26a and 26b can be attached to the second support rod 38b. Each of the first rod 38a and the second rod 38b can be attached to the third support rod 38c, such that the first and second rods 38a and 38b are fixedly secured relative to each other. Because the bone anchors 24 can be fixedly secured to the first support rod 38a, and the bone anchors 26 can be fixedly secured to the second support rod 38b, the bone anchors 24 and 26 can be fixedly secured relative to each other. While the bone anchors 24 and 26 are illustrated as being attached to the first and second support rods 38a and 38b, respectively, it should be appreciated that the bone anchors 24 and 26 can alternatively be attached and fixedly secured to a single support rod that spans across the bone gap 22c.

The external fixation system 20 can further include at least one first clamp 40 configured to attach to a first one of the bone anchors 24a-b and 26a-b, and at least one second clamp 42 configured to attach to a second one of the bone anchors 24a-b and 26a-b. The first and second clamps 40 and 42 are further configured to attach to the at least one support rod 38 so as to fixedly secure the attached bone anchors to the at least one support rod 38. In accordance with the illustrated embodiment, the at least one clamp 40 can include a first clamp 40a and a second clamp 40b that are each configured to attach to any of the bone anchors 24 and 26. In accordance with the illustrated embodiment, the first clamp 40a is attached to the first bone anchor 24a and the second clamp 40b is attached to the second bone anchor 24b. Further, in accordance with the illustrated embodiment, the at least one clamp 42 can include a first clamp 42a and a second clamp 42b that are each configured to attach to any of the bone anchors 24 and 26. In accordance with the illustrated embodiment, the first clamp 42a is attached to the first bone anchor 26a and the second clamp 42b is attached to the second bone anchor 26b. As will be appreciated from the description below, the clamps 40 and 42 are configured to attach to the respective bone anchors 24 and 26 at the respective shafts 30, for instance at the respective unthreaded external surfaces 32.

Each of the clamps 40 and 42 can be configured to attach to the at least one support rod 38. For instance, each of the clamps 40 and 42 can be configured to attach to each of the first and second support rods 38a and 38b. In accordance with the illustrated embodiment, the first clamp 40a is attached to the first support rod 38a, and the second clamp 40b is attached to the first support rod 38a. The clamps 40 can be tightened to the respective bone anchors 24 and the first support rod 38a so as to be fixedly secured to the respective bone anchors 24 and to be fixedly secured to the first support rod 38a. Further, in accordance with the illustrated embodiment, the first clamp 42a is attached to the second support rod 38b, and the second clamp 42b is attached to the second support rod 38b. The clamps 42 can be tightened to the respective bone anchors 26 and the second support rod 38b so as to be fixedly secured to the respective bone anchors 26 and to be fixedly secured to the second support rod 38b. In an embodiment where the at least one support rod 38 defines a single support rod, each of the clamps 40 and 42 can be configured to be attached and fixedly secured to the single support rod at different locations along the single support rod.

With continuing reference to FIG. 1, the external fixation assembly 20 can include a bridge 44 that is configured to fixedly secure the first and second support rods 38a and 38b relative to each other. The bridge 44 can include the third support rod 38c, a first clamp 48a configured to attach to both the third support rod 38c and the first support rod 38a, and a second clamp 48b configured to attach to both the third support rod 38c and the second support rod 38b. In particular, each of the first and second clamps 48a and 48b can define respective first and second channels 49a and 49b. The channel 49a and 49b can be oriented substantially parallel or angularly offset with respect to each other as desired, and can be sized, so as to respectively receive the third support rod 38c and a corresponding one of the first and second support rods 38a and 38b. The clamps 48a and 48b can be tightened to the respective third support rod 38c and the corresponding first and second support rods 38a and 38b, so as to fixedly secure the third support rod 38c with respect to the first and second support rods 38a and 38b, thereby fixedly securing the first and second support rods 38a and 38b to each other.

Referring now to FIGS. 2A-2B, the clamp 40a is illustrated, it being appreciated that the clamp 40a can be representative of one or more up to all of the clamps 40b and 42a-b. Thus, the description of the clamp 40a can apply to all other clamps of the external fixation system 20 as desired. The clamp 40a can include a clamp body 50 that defines first and second channels 52a and 52b. The first channel 52a is configured to receive the corresponding bone anchor, such as the bone anchor 24a, for instance at the shaft portion 30. For instance, the clamp body 50 can include a first inner surface 54 that defines the first channel 52a. The inner surface 54 can be tightened against the shaft 30 so as to fixedly secure the bone anchor 24a to the clamp 40a. In accordance with one embodiment, the inner surface 54 can be defined by first and second clamp members 56a and 56b of the clamp body 50. The first and second clamp members 56a and 56b can be biased together so as to tighten the inner surface 54 against the shaft 30. It should be appreciated that the inner surface 54 can be textured so as to increase the grip of the inner surface 54 relative to the shaft 30.

Similarly, the second channel 52b is configured to receive the at least one support rod 38, such as the corresponding first support rod 38a. For instance, the clamp body 50 can include a second inner surface 58 that defines the second channel 52b. The second inner surface 58 can be tightened against the shaft first support rod 38a so as to fixedly secure the first support rod 48a to the clamp 40a. In accordance with one embodiment, the inner surface 58 can be defined by third and fourth clamp members 60a and 60b of the clamp body 50. The third and fourth clamp members 60a and 60b can be biased together so as to tighten the inner surface 58 against the first support rod 38a. It should be appreciated that the inner surface 58 can be textured so as to increase the grip of the inner surface 58 against the shaft first support rod 38a.

In accordance with the illustrated embodiment, the clamp 40a can include a tightener 63 having a head 64 and a shaft 66 that extends out from the head 64. The shaft 66 can carry threads 68 that mate with threads 70 of a threaded surface 71 of the clamp body 50. The head 64 is sized to abut an abutment surface 73 of the clamp body 52. The first and second inner surfaces 54 and 58 can be disposed between the abutment surface 73 and the threaded surface 71. Accordingly, as the tightener 63 is rotated in a first direction relative to the clamp body 50, the abutment surface 73 and the threaded surface 71 are drawn toward each other, thereby causing the inner surfaces 54 and 58 to compress against the shaft 30 and the first support rod 38a, respectively, thereby preventing the bone anchor and the first support rod 38a from moving within the respective channels 52a and 52b relative to the clamp body 50. As the tightener 63 is rotated in a second direction relative to the clamp body 50 opposite the first direction, a gap between the head 64 and the abutment surface 73 loosens the inner surfaces 54 and 58 from the shaft 30 and the first support rod 38a, thereby allowing the bone anchor 24 and the first support rod 38a to move within the respective channels 52a and 52b.

The at least one support rod 38, including the first support rod 38a, the second support rod 38b, and the third support rod 38c, can all be made of an electrically conductive material, and can be devoid of any insulating material, for instance at least at locations at and between the first and second bone anchors described above, though it should be appreciated that the rods 38a-c can include an insulating material as desired. The clamps, 40, 42, and 48 can likewise be made from an electrically conductive material, such as stainless steel, titanium, and alloys thereof. The clamps 40, 42, and 48 can also be devoid of an insulating material, though it should be appreciated that the rods clamps 40, 42, and 48 can include an insulating material as desired. Furthermore, while the external fixation system 20 has been described in accordance with one embodiment, it is recognized that external fixation systems are available including any number of bone anchors, support rods, and corresponding clamps, as desired, defining essentially any configuration and arrangement as desired. Thus, the present disclosure is not limited to the bone fixation assembly 20 described herein.

Referring now to FIGS. 3A-B, the first bone anchor 24a is illustrated, it being appreciated that the bone anchor 24a can be representative of one or more up to all of the bone anchors 24b and 26. Thus, the description of the bone anchor 24a can apply to all other bone anchors of the external fixation system 20 as desired. The bone anchor 24 can be elongate along a central axis 25, which can define an axial direction. The bone anchor 24 can include the shaft 30 that is elongate along the central axis 25 and the threaded region 34 that extends from the shaft 30 and is elongate along the central axis 25. The external surface 32 of at least a portion of the shaft can revolve about the first central axis The bone anchor 24 can further include a tip 35 that extends from the threaded region 34. The tip 35 can be tapered, and can include at least one cutting flute that is configured to create an aperture into the bone. Alternatively, the bone anchor 24 can be devoid of cutting flutes. Thus, a hole can be pre-drilled into the bone, and the threaded region can be driven into the pre-drilled hole.

It should be appreciated that the shaft 30, the threaded region 34, and the tip (if included) can be constructed to define any suitable size and shape as desired. For instance, the shaft 30 can define a first outermost cross-sectional dimension D1, which can be a diameter, along a direction perpendicular to the central axis 25. The threaded region 34 can define a second outermost cross-sectional dimension D2, which can be a diameter, that is less than the first outermost cross-sectional dimension D1. Alternatively the first outermost cross-sectional dimension D1 can be substantially equal to the second outermost cross-sectional dimension D2. Alternatively still, the shaft 30 can include a first portion 31a that defines the first outermost cross-sectional dimension D1, and a second portion 31b that can define the second outermost cross-sectional dimension D2.

The shaft 30 defines a first terminal end, such as a proximal end 30a, and a second or distal end 30b that is spaced from and opposite the proximal end 30a along the central axis 25. The shaft 30 can define a shoulder 33 that defines an interface between the first portion 31a and the second portion 31b. The proximal end 30a can be defined by the first portion 31a, and the distal end 30b can be defined by the second portion 31b, such that the shoulder 33 is disposed between the proximal end 30a and the distal end 30b. Alternatively, the shaft 30 can be devoid of the shoulder 33, and can define a substantially constant outermost cross-sectional dimension D1 from the proximal end 30a to the distal end 30b. The proximal end 30a can define any suitable engagement member as desired that is configured to attach to a driving instrument that is configured to rotate the bone anchor 24a so as to drive the threaded region 34 into the bone.

The threaded region 34 defines a proximal end 34a and a distal end 34b that is spaced from and opposite the proximal end 34a along the central axis 25. The proximal end 34a can extend integrally and monolithically from the distal end 30b, such that the threaded region 34 is integral and monolithic with the shaft 30. The tip 35, if present, can extend from the distal end 34b so as to be integral and monolithic with each of the threaded region 34 and the shaft 30. By way of example only, the bone anchor 24a can define any length as desired along the central axis 25 from the tip to the proximal end 30a of the shaft, for instance within a range having a lower end of approximately 60 mm and an upper end of approximately 250 mm. The cross-sectional dimensions D1 and D2 can be between approximately 2 mm and approximately 8 mm, including approximately 3 mm, approximately 4 mm, and approximately 5 mm.

With continuing reference to FIGS. 3A-3C, the bone anchor 24a can include an electrically insulative material 84, which can be configured as a layer 82 of electrically insulative material 84, that can be attached to at least a portion of the external surface 32, but not to the threaded region 34. For instance, the layer 82 of electrically insulative material 84 can be adhesively attached to the at least a portion of the external surface 32. For example, the layer 82 can be attached to the external surface at a location between the shoulder 33 and the proximal end 30a. The layer 82 can, for instance, be received in the corresponding channel 52a of the clamp 40a as described above, such that the inner surface of the channel 52a is tightened to the layer 82 so as to fixedly secure the bone anchor 24a therein. Alternatively, the inner surface of the channel 52a can tighten directly to the exterior surface 32 of the shaft 30, for instance if the layer terminates at a location spaced from the inner surface of the channel 52a.

In accordance with one embodiment, the layer 82 of electrically insulative material 84 is configured as a tape 86 having a substrate 88 made from the electrically insulative material 84, and an adhesive 90 disposed on one surface 88a of the substrate 88, such that the adhesive 90 attaches to the external surface 32 so as to attach the tape 86 to the at least a portion of the external surface 32 of the shaft 30. The substrate 88, and thus the tape 86, can define the surface 88a. Further, the substrate 88, and thus the tape 86, can define a second surface 88b opposite the surface 88a, such that the tape 86 defines a thickness measured from the surface 88a to the second surface 88b along a direction perpendicular to the central axis 25. The thickness of the tape 86 can be between approximately 1 mm and approximately 6 mm, for instance between approximately 2 mm and approximately 4 mm, including approximately 2.5 mm and approximately 3.5 mm. The small thickness of the tape 86 can allow the cross-sectional dimension of the shaft 30 can be unchanged with respect to pre-existing bone anchors suitable for inclusion in external fixation systems. As a result, the shaft 30 can include the same bending stiffness and torsional stability of pre-existing bone anchors suitable for inclusion in external fixation systems without changing the material of the shaft 30. The electrically insulative material 84, and thus the tape 86, can be substantially nonporous and non-ferromagnetic. For instance, in accordance with one embodiment, the electrically insulative material 84 can be a polyimide.

The tape 86 can be wrapped around the at least a portion of the first external surface 32 at least one entire revolution about the central axis 25. For instance, as illustrated in FIG. 3A, adjacent revolutions 94 of the tape 86 along the central axis 25 can overlap each other with respect to a line that extends through the tape 86 to the central axis 25 along a direction perpendicular to the central axis. Alternatively, adjacent revolutions 94 of the tape 86 along the central axis 25 can be disposed adjacent each other along a direction parallel to the central axis 25, such that the bone anchor 24a does not define a line that extends to the central axis along a direction perpendicular to the central axis and passes through adjacent revolutions 94 of the tape 86. The tape 86 can define a proximal end 86a and a distal end 86b that can define any suitable distance therebetween along the central axis 25. For instance, as illustrated in FIG. 3B, the distance can be suitable such that the tape 86 can be wrapped one revolution 94 about the central axis 25. For instance, the taps 86 can define opposed edges 86c and 86d that can abut each other, or can overlap each other, for instance if the tape 66 extends more than one revolution 94 about the central axis 25. Thus, it can be said that the tape 86 can make at least one revolution 94 about the central axis 25 so as to attach the adhesive 90 to the external surface 32.

Furthermore, existing bone anchors can be retrofit by applying the electrically insulative material 84 to the respective shaft as described herein so as to produce the bone anchor 24a. Thus, a method can be provided for fabricating an external fixation system of the type having first and second Schanz screws, each including a shaft that defines an external surface that is devoid of threads, and a threaded region that extends from the shaft, the threaded region presenting external threads that are configured to be anchored into a first bone segment. The method can include the step of applying a layer of electrically insulative material to at least a portion of the external surface of the first Schanz screw, such that the layer of electrically insulative material is attached to the threaded region of the first Schanz screw. The electrically insulative material can comprise a substrate having first and second opposed surfaces, and an adhesive carried by the first surface, the applying step further comprises the step adhesively attaching the first surface to the at least a portion of the external surface of the first Schanz screw. The shaft of the first Schanz screw can be elongate along a central axis, and the method can further comprising the step of attaching the first surface to the at least a portion of the external surface at least one revolution about the central axis. The shaft of the second Schanz screw can be elongate along a central axis, and the method further comprising the step of attaching the first surface to at least a portion of the external surface of the second Schanz screw at least one revolution about the central axis of the second Schanz screw.

Referring to now FIG. 4, it has been found that when the external fixation system is placed in a magnetic field having a field strength of substantially 1.5 Tesla, and radiofrequency pulses are introduced into the magnetic field, for instance of the type generated during MRI imaging, none of the threaded regions 34 of the bone anchors 24 and 26 increases in temperature in a significant way (e.g., by more than six degrees Celsius) that would cause discomfort to the patient or necrosis to the anatomical tissue that surrounds the bone anchors. In fact, testing has shown little or no temperature increases.

Thus, a method can be provided for imaging a region of human anatomy 104 that includes the bone 22. The method can include the step of placing the human anatomy, and thus the bone 22, into an interior of an MRI tube 106 having a magnetic field of between 1.5 Tesla and 3.0 Tesla. The long bone 22 defines first and second bone segments 22a and 22b to which respective threaded regions of first and second bone anchors 24 and 26 are anchored. Each of the first and second bone anchors 24 and 26 are attached to at least one support rod 38 via respective first and second clamps 40 and 42. Each of the bone anchors includes an unthreaded electrically conductive shaft 30 extending from the respective threaded regions, and an electrically insulative tape wrapped around at least a portion of each of the shafts. The method can further include the step of directing radio frequency pulses into the interior of the MRI tube so as to provide magnetic resonance images of the human anatomy, wherein the threaded regions of the bone anchors 24 and 26 do not increase in temperature by more than six degrees Celsius.

Without being bound by theory, it is believed that the bone anchors of conventional external fixation systems can be heated from three different mechanisms, including 1) eddy currents, 2) RF resonance, and 3) induction loops. With respect to RF resonance, it is believed that bone anchor heating by eddy currents of conventional external fixation systems can generate only a few degrees Celsius temperature rise. It is further believed that the electrically insulting polyimide tape disrupts both RF resonance and the formation of induction loops. Without being bound by theory, it is postulated that the electrically insulative material 84 can have a sufficiently high dielectric constant on the bone anchors 24 so as to isolate the standing RF wave pattern that resonates on the exterior conducting surface 34 of the bone anchors. Thus, it is postulated that a highly insulating material like polyimide can store electrical energy like a capacitor, the electrical current can oscillate within the capacitor, and electrical current will be disrupted, thereby eliminating RF heating at the threaded region 34 and the tip 35. Experiments have shown that a polyamide insulator can block current flow up to 3000 volts and is, therefore, capable of insulating the electrical flow responsible for RF resonance heating during magnetic resonance imaging. MRI. With respect to induction loops, and again without being bound by theory, it is believed that the polyimide insulator also can provide a low capacitance to limit the RF electrical current flowing as a loop defined by first and second Schanz screws, a support rod, clamps that secure the Schanz screws to the support rod, and the anatomical tissue that receives the bone anchors. This was evaluated by measuring the temperature rise for an external fixation system having the insulating polyimide tape applied to the first Schanz screw and no insulating polyimide tape applied to the second Schanz screw. No temperature rise was recorded at the tip of the Schanz screw that included the polyimide tape, but a temperature rise was recorded at the tip of the Schanz screw that was not taped. Accordingly, it is believed that a conductive current loop was present when only one Schanz screw included the polyimide electrical insulator.

While the foregoing description and drawings represent the preferred embodiments of the present invention, it will be understood that various additions, modifications, combinations and/or substitutions may be made therein without departing from the spirit and scope of the invention as defined in the accompanying claims. In particular, it will be clear to those skilled in the art that the invention may be embodied in other specific forms, structures, arrangements, proportions, and with other elements, materials, and components, without departing from the spirit or essential characteristics thereof. One skilled in the art will appreciate that the invention may be used with many modifications of structure, arrangement, proportions, materials, and components, which are particularly adapted to specific environments and operative requirements without departing from the principles of the invention. For instance, while the bone anchors 24 and 26 have been identified as Schanz screws in accordance with one embodiment, it is contemplated that the electrically insulative material 84 can be applied to any suitable alternative bone anchor of other types of implant assemblies, including K-wires, Steinmann pins, cranial fixation members, cranial traction tongs, and bone segment transport devices (for instance Ilizarov type). Furthermore, it should be appreciated that the electrically insulative material 84 can be configured as, or included in, a paint, a polymer, a ceramic, and a composite. Thus, the electrically insulative material 84 can be applied to the bone anchors, for instance Schanz screws, K-wires, and Steinmann pins, by conventional spraying, dipping, fluidized bed, electrostatic spraying, or any suitable alternative deposition method. In addition, features described herein may be used singularly or in combination with other features. For example, features described in connection with one embodiment may be used and/or interchanged with features described in another embodiment. The presently disclosed embodiments are therefore to be considered in all respects as illustrative and not restrictive, the scope of the invention being indicated by the appended claims, and not limited to the foregoing description.

It will be appreciated by those skilled in the art that various modifications and alterations of the invention can be made without departing from the broad scope of the appended claims. Some of these have been described above and others will be apparent to those skilled in the art.

What is claimed:

1. An external fixation system comprising:
a first external fixation bone anchor including a first shaft defining a first external surface that is devoid of threads, the first external fixation bone anchor further including a first threaded region that extends from the first shaft, the first threaded region presenting external threads that are configured to be anchored into bone, and the first external fixation bone anchor including an electrically insulative material that is attached to at least a portion of the first external surface and that is not attached to the first threaded region;
a second external fixation bone anchor defining a second shaft having a second external surface that is devoid of threads, the second external fixation bone anchor further defining a second threaded region that extends from the second shaft, the second threaded region presenting external threads that are configured to be anchored into bone;
at least one support rod comprising an electrically conductive material; and
a first clamp configured to attach to both the at least one support rod and the first shaft at the electrically insulative material, and a second clamp configured to attach to both the second shaft and the at least one support rod, thereby fixedly supporting each of the first and second external fixation bone anchors relative to the at least one support rod, wherein the first external fixation bone anchor includes the electrically insulative material prior to attachment of the first clamp to the first shaft, and wherein the electrically insulative layer comprises a tape having a substrate made from the electrically insulative material, and an adhesive disposed on one surface of the substrate, wherein the adhesive attached the tape to the at least a portion of the first external surface of the first shaft.

2. The external fixation system as recited in claim 1, wherein the first clamp is configured to attach to the at least a portion of the first external surface of the first shaft.

3. The external fixation system as recited in claim 1, wherein the first and second external fixation bone anchors comprise Schanz screws.

4. The external fixation system as recited in claim 3, wherein the electrically insulative layer is adhesively attached to the at least a portion of the first external surface of the first shaft.

5. The external fixation system as recited in claim 1, wherein the tape is nonporous.

6. The external fixation system as recited in claim 5, wherein the electrically insulative material comprises a polyimide.

7. The external fixation system as recited in claim 1, wherein the first shaft is elongate along a first central axis, the first external surface revolves about the first central axis, and the tape is wrapped around the at least a portion of the first external surface at least one entire revolution about the first central axis.

8. The external fixation system as recited in claim 7, wherein the second shaft is elongate along a second central axis, the second external surface revolves about the second central axis, and the tape is wrapped around at least a portion of the second external surface at least one entire revolution about the first central axis without extending to the second threaded region.

9. The external fixation system as recited in claim 8, wherein each of the first and second Schanz screws comprises a titanium, a stainless steel, or alloys thereof.

10. The external fixation system as recited in claim 8, wherein when the external fixation system is placed in a magnetic field having a field strength of substantially 1.5 Tesla, and radio frequency pulses are introduced into the magnetic field, neither the first threaded region nor the second threaded region increases in temperature by more than six degrees Celsius.

11. The external fixation system as recited in claim 1, wherein the first shaft has a diameter that is between 2 mm and 8 mm.

12. The external fixation system as recited in claim 11, wherein the tape defines a second surface opposite the one surface, and a thickness measured from the one surface to the second surface, the thickness being between 1 mm and 6 mm.

13. The external fixation system as recited in claim 1, wherein the at least one support rod comprises a single support rod, and each of the first and second clamps are configured to be attached to different locations along the single support rod.

14. The external fixation system as recited in claim 13, wherein the at least one support rod comprises a first support rod and a second support rod, the first clamp is configured to be attached to the first support rod, the second clamp is configured to be attached to the second support rod, and a bridge that attaches to each of the first and second support rods so as to fixedly secure the first and second support rods relative to each other.

\* \* \* \* \*